US 6,551,802 B2

(12) United States Patent
Khosla et al.

(10) Patent No.: US 6,551,802 B2
(45) Date of Patent: Apr. 22, 2003

(54) METHODS FOR MAKING POLYKETIDES (75) Inventors: Chaitan Khosla, Palo Alto, CA (US); Janice Lau, Stanford, CA (US); Nicola L. Pohl, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 59 days.

(21) Appl. No.: 09/735,685

(22) Filed: Dec. 12, 2000

(65) Prior Publication Data
US 2001/0051356 A1 Dec. 13, 2001

Related U.S. Application Data (62) Division of application No. 09/346,860, filed on Jul. 2, 1999, now Pat. No. 6,221,641.
(60) Provisional application No. 60/091,610, filed on Jul. 2, 1998, and provisional application No. 60/091,526, filed on Jul. 2, 1998.

(51) Int. Cl.[7] ................................................. C12P 19/62
(52) U.S. Cl. ............................................ 435/76; 435/183
(58) Field of Search .................................... 435/183, 76

(56) References Cited

U.S. PATENT DOCUMENTS

| 5,672,491 A | 9/1997 | Khosla et al. ............... 435/148 |
| 5,962,290 A | 10/1999 | Khosla et al. ............... 435/183 |

FOREIGN PATENT DOCUMENTS

| GB | WO 98/01546 | 1/1998 |
| WO | WO 97/02358 | 1/1997 |
| WO | WO 98/49315 | 11/1997 |
| WO | WO 99/03986 | 1/1999 |

OTHER PUBLICATIONS

Bohm I., et al. (1998). "Engineering of a minimal modular polyketide synthase, and targeted alteration of the stereospecificity of polyketide chain extension," *Chemistry and Biology* 5 (6):407–412.
Haydock et al. (1995) *FEBS Letters* 374:246–248.
Kakavas et al. (1997) 179(23):7515–7522.
Kao, C.M. et al. (1996). "Evidence for two catalytycally independent clusters of active sites in a functional modular polyketide synthase," *Biochemistry* 35(38):12363–12368.
Katz, L. (1997). "Manipulation of modular polyketide synthases," *Chemical Reviews* 97(7):2557–2575.
Khosla (1977) *Chem. Rev.* 97:2577–2590.
Khosla, C. et al. (1999). "Tolerance and specificity of polyketide synthases," *Annual Review of Biochemistry* 68:219–253.

(List continued on next page.)

*Primary Examiner*—Nashaat T. Nashed
(74) *Attorney, Agent, or Firm*—Morrison & Foerster LLP; Kate H. Murashige; David Lentini (57) ABSTRACT

The stereochemical centers of a polyketide can be changed by replacement of ketosynthase domains in the polyketide synthase (PKS) enzyme that produces the polyketide. The specificity of the AT domains of a PKS is determined by a hypervariable region that can be replaced or altered to change the specificity of the AT domain from a naturally occurring extender unit to another naturally or non-naturally occurring extender unit. Non-naturally occurring extender units, including methylmalonyl N-acetyl cysteamine thioester can be incorporated into polyketides in recombinant host cells or in cell-free systems to make polyketides.

7 Claims, 3 Drawing Sheets

```
                    NheI                                Styl
DEBS LOAD AT:  FVEASPHPV  LAAALQQTL.   DAEGSSAAVV  PTLQRGQ . GG MRRFLLAAA.   ... QAFTGG    Propionyl AT
DEBS AT2:      FIEVSPHPV  LASSVQETLD   DAE.SDAAVL  GTLERDA . GD ADRFLTALA.   ... DAHTRG  ⎤
NID AT4:       FVECSPHPV  LTVPVRQTLE   DA.GAGAVAV  GSLRRDD. GG LRRFLTSAA.    ... EAQVAG
FK506 AT9:     FIECSAHPV  LLPAL......  DQE. RT ...V ASLRTDD . GG WDRFLTALA.  ... QAWTQGK   Methylmalonyl
RAPS AT1:      FVEVSASPV  LLQAM......  DDDVVT ...V ATLRRDD . GD ATRMLTALA.   ... QAYVEG      AT
RIF AT1:       FVEVSAHPV  TVQPL......  SE ... LTGDAI GTLRRED . GG LRR. L .. LA. SMGELFVRG
DEBS AT6:      FVEMSPHPV  LTAAVQEIAA   D ...... AVAI GSLHRDT. AE . EHLIAELA.  ... RAHVHG  ⎦
NID AT5:       FLETSPHPM  LAVALEQTVT   DA. GTDAAVL GTLRRRH . GG PRA. LA. LA. .VCRFAFAHG   Ethylmalonlyl AT
NID LOAD AT:   YLEIGPHPT  LTTLLHHTLD   NP .. TT....I PTLHRER . PE PETLTQAIAA. .. VG. VRTDG    Acetyl AT
NID AT1:       YLEIGAHPT  LTTLLHHTLD   NP .. TT....I PTLHREH . PE PETLTALAT.  .....LHTTG  ⎤
FK506 AT7:     FLEIGPNQD  LSPVVDG....  .........I PTQTGTP . EE VQALHTALA.    ... RLHTRG
FK506 AT8:     FVEIGPGQD  LSPLVDG....  .........I ALQNGTA . DE VEALHTALA.    ... RLFTRG    Malony AT
RAPS AT2:      FVELGADRS  LARLVDG....  .........I AMLHGD . HE AQAAVGALA.    ... HLYVNG
RIF AT2:       FLELGPGGA  LAAMALGTLG GPEQSC...V ATLRKNG . AE VPDVLTALA.     ... ELHVRG
E. COLI FAS:   Y. EVGPGKV LT.........  GL TKRIV DTLTASALNE  PSAMAAALE.     .... L~~~~ ⎦
```

OTHER PUBLICATIONS

Kuhstoss, S. et al. (1996). "Production of a novel polyketide through the construction of a hybrid polyketide synthase," *Gene* 183(1):231–236.

Lau et al., 1999, "Dissecting the Role of Acyltransferase Domains of Modular Polyketide Synthases in the Choice and Stereochemical Fate of Extender Units", *Biochemistry* 38(5):1643–51.

Lau, J. et al. (1998). "Dissecting and manipulating substrate specificity of the acyltransferase domains of modular polyketide synthases," Book of Abstracts, 216th ACS National Meeting, Boston, Aug. 23–27,BTEC–028.

Marsden, A.F. et al. (1994). "Stereospecific acyl transfers on the erythromycin–producing polyketide synthase," *Science* 263(5145):378–380.

Miller, W.W. et al. (1968). "N–acetyl–S–methylmalonylcysteamine, an inhibitor of methylmalonyl coenzyme A isomerase," *Biochem Biophys Res Commun* 33(4):1569–1573.

Motamedi et al. (1997) *Eur. J. Biochem.* 244:74–80.

Oliynyk et al. (1996) *Chem. & Biol.* 3:833–839.

Pohl et al., 1998, "Synthesis and Incorporation of an N–Acetylcysteamine Analogue of Methylmalonyl–CoA by a Modular Polyketide Synthase", *J. Am. Chem. Soc.,* 120:11206–7.

Ruan et al. (1997) *J. Bacteriol.* 179(20):6416–6425.

Schwecke et al. (1995) "The Biosynthetic Gene Cluster for the Polyketide Immunosuppressant Rapamycin," *PNAS,* 92:7839–7843.

Staunton et al. (1997) Chem. Rev. 97(7):2611–2630.

Stassi, D.L. et al. (1998). "Ethyl–substituted erythromycin derivatives produced by directed metabolic engineering," *Proc Natl Acad Sci* USA 95(13):7305–7309.

Weissman, K.J. et al. (1997). "The molecular basis of Celmer's rules: the stereochemistry of the condensation step in chain extension on the erythromycin polyketide synthase," *Biochemistry* 36(45):13849–13855.

|  | NheI | | | StyI | | |
|---|---|---|---|---|---|---|
| DEBS LOAD AT: | FVEASPHPV | LAAALQQTL. | DAEGSSAAVV | PTLQRGQ. GG | MRRFLLAAA. | ... QAFTGG | Propionyl AT |
| DEBS AT2: | FIEVSPHPV | LASSVQETLD | DAE.SDAAVL | GTLERDA. GD | ADRFLTALA. | ... DAHTRG | |
| NID AT4: | FVECSPHPV | LTVPVRQTLE | DA.GAGAVAV | GSLRRDD. GG | LRRFLTSAA. | ... EAQVAG | |
| FK506 AT9: | FIECSAHPV | LLPAL...... | DQE. RT... V | ASLRTDD. GG | WDRFLTALA... | QAWTQGK | Methylmalonyl AT |
| RAPS AT1: | FVEVSASPV | LLQAM...... | DDDVVT... V | ATLRRDD. GD | ATRMLTALA. | ... QAYVEG | |
| RIF AT1: | FVEVSAHPV | TVQPL...... | SE ... LTGDAI | GTLRRED. GG | LRR. L.. LA. | SMGELFVRG | |
| DEBS AT6: | FVEMSPHPV | LTAAVQEIAA | D....... AVAI | GSLHRDT. AE | . EHLIAELA. | ... RAHVHG | |
| NID AT5: | FLETSPHPM | LAVALEQTVT | DA. GTDAAVL | GTLRRRH. GG | PRA. LA. LA.. | VCRFAFAHG | Ethylmalonyl AT |
| NID LOAD AT: | YLEIGPHPT | LTTLLHHTLD | NP.. TT..... I | PTLHRER. PE | PETLTQAIAA.. | VG. VRTDG | Acetyl AT |
| NID AT1: | YLEIGAHPT | LTTLLHHTLD | NP.. TT..... I | PTLHREH. PE | PETLTTALAT. | ..... LHTG | |
| FK506 AT7: | FLEIGPNQD | LSPWDG..... | ........... I | PTQTGTP . EE | VQALHTALA. | .... RLHTRG | |
| FK506 AT8: | FVEIGPGQD | LSPLVDG.... | ........... I | ALQNGTA . DE | VEALHTALA. | .... RLFTRG | Malony AT |
| RAPS AT2: | FVELGADRS | LARLVDG.... | ........... I | AMLHGD . HE | AQAAVGALA. | .... HLYVNG | |
| RIF AT2: | FLELGPGGA | LAAMALGTLG | GPEQSC.... V | ATLRKNG . AE | VPDVLTALA. | ... ELHVRG | |
| E. COLI FAS: | Y. EVGPGKV | LI.......... | ..... GL TKRIV | DTLTASALNE | PSAMAAALE. | ..... L~~~ | |

```
                         SEQUENCE LISTING

<160> NUMBER OF SEQ ID NOS: 15

<210> SEQ ID NO 1
<211> LENGTH: 52
<212> TYPE: PRT
<213> ORGANISM: Saccharopolyspora erythraea

<400> SEQUENCE: 1

Phe Val Glu Ala Ser Pro His Pro Val Leu Ala Ala Ala Leu Gln Gln
 1               5                  10                  15

Thr Leu Asp Ala Glu Gly Ser Ser Ala Ala Val Val Pro Thr Leu Gln
            20                  25                  30

Arg Gly Gln Gly Gly Met Arg Arg Phe Leu Leu Ala Ala Ala Gln Ala
        35                  40                  45

Phe Thr Gly Gly
    50

<210> SEQ ID NO 2
<211> LENGTH: 52
<212> TYPE: PRT
<213> ORGANISM: Saccharopolyspora erythraea

<400> SEQUENCE: 2

Phe Ile Glu Val Ser Pro His Pro Val Leu Ala Ser Ser Val Gln Glu
 1               5                  10                  15

Thr Leu Asp Asp Ala Glu Ser Asp Ala Ala Val Leu Gly Thr Leu Glu
            20                  25                  30

Arg Asp Ala Gly Asp Ala Asp Arg Phe Leu Thr Ala Leu Ala Asp Ala
        35                  40                  45

His Thr Arg Gly
    50

<210> SEQ ID NO 3
<211> LENGTH: 52
<212> TYPE: PRT
<213> ORGANISM: Streptomyces sp.

<400> SEQUENCE: 3

Phe Val Glu Cys Ser Pro His Pro Val Leu Thr Val Pro Val Arg Gln
 1               5                  10                  15

Thr Leu Glu Asp Ala Gly Ala Gly Ala Val Ala Val Gly Ser Leu Arg
            20                  25                  30

Arg Asp Asp Gly Gly Leu Arg Arg Phe Leu Thr Ser Ala Ala Glu Ala
        35                  40                  45

Gln Val Ala Gly
    50

<210> SEQ ID NO 4
<211> LENGTH: 44
<212> TYPE: PRT
<213> ORGANISM: Streptomyces sp.
```

-continued

```
<400> SEQUENCE: 4

Phe Ile Glu Cys Ser Ala His Pro Val Leu Leu Pro Ala Leu Asp Gln
  1               5                  10                  15

Glu Arg Thr Val Ala Ser Leu Arg Thr Asp Asp Gly Gly Trp Asp Arg
             20                  25                  30

Phe Leu Thr Ala Leu Ala Gln Ala Trp Thr Gln Gly
         35                  40

<210> SEQ ID NO 5
<211> LENGTH: 45
<212> TYPE: PRT
<213> ORGANISM: Streptomyces sp.

<400> SEQUENCE: 5

Phe Val Glu Val Ser Ala Ser Pro Val Leu Leu Gln Ala Met Asp Asp
  1               5                  10                  15

Asp Val Val Thr Val Ala Thr Leu Arg Arg Asp Asp Gly Asp Ala Thr
             20                  25                  30

Arg Met Leu Thr Ala Leu Ala Gln Ala Tyr Val Glu Gly
         35                  40                  45

<210> SEQ ID NO 6
<211> LENGTH: 46
<212> TYPE: PRT
<213> ORGANISM: Actinomyces sp.

<400> SEQUENCE: 6

Phe Val Glu Val Ser Ala His Pro Val Thr Val Gln Pro Leu Ser Glu
  1               5                  10                  15

Leu Thr Gly Asp Ala Ile Gly Thr Leu Arg Arg Glu Asp Gly Gly Leu
             20                  25                  30

Arg Arg Leu Leu Ala Ser Met Gly Glu Leu Phe Val Arg Gly
         35                  40                  45

<210> SEQ ID NO 7
<211> LENGTH: 47
<212> TYPE: PRT
<213> ORGANISM: Saccharopolyspora erythraea

<400> SEQUENCE: 7

Phe Val Glu Met Ser Pro His Pro Val Leu Thr Ala Ala Val Gln Glu
  1               5                  10                  15

Ile Ala Ala Asp Ala Val Ala Ile Gly Ser Leu His Arg Asp Thr Ala
             20                  25                  30

Glu Glu Lys Leu Ile Ala Glu Leu Ala Arg Ala His Val His Gly
         35                  40                  45

<210> SEQ ID NO 8
<211> LENGTH: 52
<212> TYPE: PRT
<213> ORGANISM: Streptomyces sp.

<400> SEQUENCE: 8

Phe Leu Glu Thr Ser Pro His Pro Met Leu Ala Val Ala Leu Glu Gln
  1               5                  10                  15

Thr Val Thr Asp Ala Gly Thr Asp Ala Ala Val Leu Gly Thr Leu Arg
             20                  25                  30

Arg Arg His Gly Gly Pro Arg Ala Leu Ala Leu Ala Val Cys Arg Ala
         35                  40                  45
```

```
Phe Ala His Gly
     50

<210> SEQ ID NO 9
<211> LENGTH: 50
<212> TYPE: PRT
<213> ORGANISM: Streptomyces sp.

<400> SEQUENCE: 9

Tyr Leu Glu Ile Gly Pro His Pro Thr Leu Thr Thr Leu Leu His His
 1               5                  10                  15

Thr Leu Asp Asn Pro Thr Thr Ile Pro Thr Leu His Arg Glu Arg Pro
                20                  25                  30

Glu Pro Glu Thr Leu Thr Gln Ala Ile Ala Val Gly Val Arg Thr
            35                  40                  45

Asp Gly
     50

<210> SEQ ID NO 10
<211> LENGTH: 48
<212> TYPE: PRT
<213> ORGANISM: Streptomyces sp.

<400> SEQUENCE: 10

Tyr Leu Glu Ile Gly Ala His Pro Thr Leu Thr Thr Leu Leu His His
 1               5                  10                  15

Thr Leu Asp Asn Pro Thr Thr Ile Pro Thr Leu His Arg Glu His Pro
                20                  25                  30

Glu Pro Glu Thr Leu Thr Thr Ala Leu Ala Thr Leu His Thr Thr Gly
            35                  40                  45

<210> SEQ ID NO 11
<211> LENGTH: 41
<212> TYPE: PRT
<213> ORGANISM: Streptomyces sp.

<400> SEQUENCE: 11

Phe Leu Glu Ile Gly Pro Asn Gln Asp Leu Ser Pro Val Val Asp Gly
 1               5                  10                  15

Ile Pro Thr Gln Thr Gly Thr Pro Glu Glu Val Gln Ala Leu His Thr
                20                  25                  30

Ala Leu Ala Arg Leu His Thr Arg Gly
            35                  40

<210> SEQ ID NO 12
<211> LENGTH: 41
<212> TYPE: PRT
<213> ORGANISM: Streptomyces sp.

<400> SEQUENCE: 12

Phe Val Glu Ile Gly Pro Gly Gln Asp Leu Ser Pro Leu Val Asp Gly
 1               5                  10                  15

Ile Ala Leu Gln Asn Gly Thr Ala Asp Glu Val Glu Ala Leu His Thr
                20                  25                  30

Ala Leu Ala Arg Leu Phe Thr Arg Gly
            35                  40

<210> SEQ ID NO 13
<211> LENGTH: 40
<212> TYPE: PRT
<213> ORGANISM: Streptomyces sp.
```

```
<400> SEQUENCE: 13

Phe Val Glu Leu Gly Ala Asp Arg Ser Leu Ala Arg Leu Val Asp Gly
 1               5                  10                  15

Ile Ala Met Leu His Gly Asp His Glu Ala Gln Ala Ala Val Gly Ala
                20                  25                  30

Leu Ala His Leu Tyr Val Asn Gly
            35                  40

<210> SEQ ID NO 14
<211> LENGTH: 50
<212> TYPE: PRT
<213> ORGANISM: Actinomyces sp.

<400> SEQUENCE: 14

Phe Leu Glu Leu Gly Pro Gly Gly Ala Leu Ala Ala Met Ala Leu Gly
 1               5                  10                  15

Thr Leu Gly Gly Pro Glu Gln Ser Cys Val Ala Thr Leu Arg Lys Asn
                20                  25                  30

Gly Ala Glu Val Pro Asp Val Leu Thr Ala Leu Ala Glu Leu His Val
            35                  40                  45
Arg Gly
      50

<210> SEQ ID NO 15
<211> LENGTH: 37
<212> TYPE: PRT
<213> ORGANISM: E. coli

<400> SEQUENCE: 15

Tyr Glu Val Gly Pro Gly Lys Val Leu Thr Gly Leu Thr Lys Arg Ile
 1               5                  10                  15

Val Asp Thr Leu Thr Ala Ser Ala Leu Asn Glu Pro Ser Ala Met Ala
                20                  25                  30

Ala Ala Leu Glu Leu
            35
```

METHODS FOR MAKING POLYKETIDES

CROSS-REFERENCE TO RELATED APPLICATIONS

This application is a divisional of U.S. Ser. No. 09/346,860 filed Jul. 2, 1999, and now U.S. Pat. No. 6,221,641, which application claims priority to Ser. Nos. 60/091,526 and 60/091,610, both filed Jul. 2, 1998, and both of which are incorporated herein by reference in their entirety.

REFERENCE TO GOVERNMENT FUNDING

This invention was supported in part by grants from the National Institutes of Health (CA-66736 and GM-22172). The U.S. government has certain rights in this invention.

FIELD OF THE INVENTION

The present invention relates to polyketides and the polyketide synthase (PKS) enzymes that produce them. The invention also relates generally to genes encoding PKS enzymes and to recombinant host cells containing such genes and in which expression of such genes leads to the production of polyketides. Thus, the invention relates to the fields of chemistry, molecular biology, and agricultural, medical, and veterinary technology.

BACKGROUND OF THE INVENTION

Polyketides are a class of compounds synthesized from 2-carbon units through a series of condensations and subsequent modifications. Polyketides occur in many types of organisms, including fungi and mycelial bacteria, in particular, the actinomycetes. Polyketides are biologically active molecules with a wide variety of structures, and the class encompasses numerous compounds with diverse activities. Tetracycline, erythromycin, epothilone, FK-506, FK-520, narbomycin, picromycin, rapamycin, spinocyn, and tylosin are examples of polyketides. Given the difficulty in producing polyketide compounds by traditional chemical methodology, and the typically low production of polyketides in wild-type cells, there has been considerable interest in finding improved or alternate means to produce polyketide compounds.

The biosynthetic diversity of polyketides is generated by repetitive condensations of simple monomers by PKSs that mimic fatty acid synthases but are capable of additional processing reactions (see Carreras et al., 1997, Topic in Current Chemistry, Springer-Verlag, Berlin; and Staunton et al., 1997, Chem. Rev. 97: 2611–2629, each of which is incorporated herein by reference). For instance, the deoxyerythronolide-B (DEBS-B) synthase catalyzes the chain extension of a primer with several methylmalonyl coenzyme A (MeMalCoA) extender units to produce the erythromycin core (see Khosla, 1997, Chem. Rev. 97: 2577–2590, and Hopwood, 1997, Chem. Rev. 97: 2465–2495, each of which is incorporated herein by reference).

The cloning, analysis, and recombinant DNA technology of genes that encode PKS enzymes allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. See, e.g., PCT publication Nos. WO 93/13663; 95/08548; 96/40968; 97/02358; 98/27203; and 98/49315; U.S. Pat. Nos. 4,874,748; 5,063,155; 5,098,837; 5,149,639; 5,672,491; 5,712,146; 5,830,750; and 5,843,718; and Fu et al., 1994, Biochemistry 33: 9321–9326; McDaniel et al., 1993, Science 262: 1546–1550; and Rohr, 1995, Angew. Chem. Int. Ed. Engl. 34(8): 881–888, each of which is incorporated herein by reference.

PKSs catalyze the biosynthesis of polyketides through repeated, decarboxylative Claisen condensations between acylthioester building blocks. The building blocks used to form complex polyketides are typically acylthioesters, such as acetyl, butyryl, propionyl, malonyl, hydroxymalonyl, methylmalonyl, and ethylmalonyl CoA. Two major types of PKS enzymes are known; these differ in their composition and mode of synthesis of the polyketide synthesized. These two major types of PKS enzymes are commonly referred to as Type I or "modular" and Type II "iterative" PKS enzymes.

In the Type I or modular PKS enzyme group, a set of separate catalytic active sites (each active site is termed a "domain", and a set thereof is termed a "module") exists for each cycle of carbon chain elongation and modification in the polyketide synthesis pathway. The typical modular PKS is composed of several large polypeptides, which can be segregated from amino to carboxy terminii into a loading module, multiple extender modules, and a releasing (or thioesterase) domain. The PKS enzyme known as 6-deoxyerythronolide B synthase (DEBS) is a typical Type I PKS. In DEBS, there is a loading module, six extender modules, and a thioesterase (TE) domain. The loading module, six extender modules, and TE of DEBS are present on three separate proteins (designated DEBS-1, DEBS-2, and DEBS-3, with two extender modules per protein). Each of the DEBS polypeptides is encoded by a separate open reading frame (ORF) or gene; these genes are known as eryAI, eryAII, and eryAIII. See Caffrey et al., 1992, FEBS Letters 304: 205, and U.S. Pat. No. 5,824,513, each of which is incorporated herein by reference. (See FIG. 2.) There is considerable interest in the genetic and chemical reprogramming of modular PKSs (see, e.g., Khosla, 1997, Chem. Rev. 97: 2577–2590, and Staunton et al., 1997, Chem. Rev. 97: 2611–2629, each of which is incorporated herein by reference).

Generally, the loading module is responsible for binding the first building block used to synthesize the polyketide and transferring it to the first extender module. The loading module of DEBS consists of an acyltransferase (AT) domain and an acyl carrier protein (ACP) domain. Another type of loading module utilizes an inactivated KS, an AT, and an ACP. This inactivated KS is in some instances called $KS^Q$, where the superscript letter is the abbreviation for the amino acid, glutamine, that is present instead of the active site cysteine required for ketosynthase activity. In other PKS enzymes, including the FK-520 PKS, the loading module incorporates an unusual starter unit and is composed of a CoA ligase activity domain. In any event, the loading module recognizes a particular acyl-CoA (usually acetyl or propionyl but sometimes butyryl) and transfers it as a thiol ester to the ACP of the loading module.

The AT on each of the extender modules recognizes a particular extender-CoA (malonyl or alpha-substituted malonyl, i.e., methylmalonyl, ethylmalonyl, and carboxylglycolyl) and transfers it to the ACP of that extender module to form a thioester. Each extender module is responsible for accepting a compound from a prior module, binding a building block, attaching the building block to the compound from the prior module, optionally performing one or more additional functions, and transferring the resulting compound to the next module.

Each extender module of a modular PKS contains a ketosynthase (KS), AT, ACP, and zero, one, two, or three enzymes that modify the beta-carbon of the growing polyketide chain. A typical (non-loading) minimal Type I PKS extender module is exemplified by extender module three of DEBS, which contains a KS domain, an AT domain, and an ACP domain. These three domains are sufficient to activate a 2-carbon extender unit and attach it to the growing polyketide molecule. The next extender module, in turn, is responsible for attaching the next building block and transferring the growing compound to the next extender module until synthesis is complete.

Once the PKS is primed with acyl- and malonyl-ACPs, the acyl group of the loading module migrates to form a thiol ester (trans-esterification) at the KS of the first extender module; at this stage, extender module one possesses an acyl-KS adjacent to a malonyl (or substituted malonyl) ACP. The acyl group derived from the loading module is then covalently attached to the alpha-carbon of the malonyl group to form a carbon—carbon bond, driven by concomitant decarboxylation, and generating a new acyl-ACP that has a backbone two carbons longer than the loading building block (elongation or extension).

The polyketide chain, growing by two carbons each extender module, is sequentially passed as covalently bound thiol esters from extender module to extender module, in an assembly line-like process. The carbon chain produced by this process alone would possess a ketone at every other carbon atom, producing a polyketone, from which the name polyketide arises. Most commonly, however, additional enzymatic activities modify the beta keto group of each two carbon unit just after it has been added to the growing polyketide chain but before it is transferred to the next module.

Thus, in addition to the minimal module containing KS, AT, and ACP domains necessary to form the carbon—carbon bond and as noted above, modules may contain a ketoreductase (KR) domain that reduces the keto group to an alcohol. Modules may also contain a KR domain plus a dehydratase (DH) domain that dehydrates the alcohol to a double bond. Modules may also contain a KR domain, a DH domain, and an enoylreductase (ER) domain that converts the double bond product to a saturated single bond using the beta carbon as a methylene function. An extender module can also contain other enzymatic activities, such as, for example, a methylase or dimethylase activity.

After traversing the final extender module, the polyketide encounters a releasing domain that cleaves the polyketide from the PKS and typically cyclizes the polyketide. For example, final synthesis of 6-dEB is regulated by a TE domain located at the end of extender module six. In the synthesis of 6-dEB, the TE domain catalyzes cyclization of the macrolide ring by formation of an ester linkage. In FK-506, FK-520, rapamycin, and similar polyketides, the ester linkage formed by the TE activity is replaced by a linkage formed by incorporation of a pipecolate acid residue. The enzymatic activity that catalyzes this incorporation for the rapamycin enzyme is known as RapP, encoded by the rapP gene. The polyketide can be modified further by tailoring enzymes; these enzymes add carbohydrate groups or methyl groups, or make other modifications, i.e., oxidation or reduction, on the polyketide core molecule. For example, 6-dEB is hydroxylated at C6 and C12 and glycosylated at C3 and C5 in the synthesis of erythromycin A.

In PKS polypeptides, the regions that encode enzymatic activities (domains) are separated by linker or "scaffold"-encoding regions. These scaffold regions encode amino acid sequences that space the domains at the appropriate distances and in the correct order. Thus, the linker regions of a PKS protein collectively can be considered to encode a scaffold into which the various domains (and thus modules) are placed in a particular order and spatial arrangement. Generally, this organization permits PKS domains of different or identical substrate specificities to be substituted (usually at the DNA level) between PKS enzymes by various available methodologies. Thus, there is considerable flexibility in the design of new PKS enzymes with the result that known polyketides can be produced more effectively, and novel polyketides useful as pharmaceuticals or for other purposes can be made.

There remains a need for new methods and reagents for making polyketides. In particular, methods for altering the stereochemistry of polyketides by altering the PKS enzymes that produce the polyketides, as well as methods for altering the specificity of AT domains of PKS enzymes, without substantial loss of PKS activity are needed. The present invention helps meet the need for such nucleic acid compounds by providing new methods and reagents for manipulating PKS genes.

DISCLOSURE OF THE INVENTION

In one embodiment, the invention provides a method for altering the specificity of an acyltransferase (AT) domain of a polyketide synthase, which method comprises the step of altering the amino acid sequence of the hypervariable region of the AT domain without changing at least a portion of the remaining AT domain amino acid sequence. In one embodiment, the specificity of the AT domain is changed from one naturally occurring starter or extender unit to another. The correct specificity may, if desired, be assured by altering the hypervariable region to mimic that of an AT of the desired specificity such as those shown in FIG. 1.

In another embodiment, the invention provides a method for changing the specificity of an AT domain of a PKS including changing it from that for the naturally occurring starter or extender unit to a starter or extender unit that is not naturally incorporated, said method comprising the steps of altering the amino acid sequence of the hypervariable region of the AT domain by mutagenesis, and if necessary, assessing the resulting specificity by contacting the PKS comprising the altered AT domain with one or more starter or extender units that are not incorporated into polyketides in nature, and identifying whether the altered AT domain can incorporate the tested starter or extender unit. In related embodiments, the invention provides novel PKS enzymes capable of incorporating starter or extender units not natively incorporated and novel polyketides produced thereby.

In another embodiment, the present invention provides non-native extender substrates for PKS enzymes and methods of making such extender substrates. In one embodiment, these non-native extender substrates are used to make polyketides in a cell-free system and in host cells that do not naturally produce polyketides but which can produce polyketides when provided with a recombinant PKS and the appropriate substrates.

In another embodiment, the invention provides a method for altering the stereochemistry of a polyketide by replacing a KS domain in the PKS that produces the polyketide with a KS domain that provides the desired stereochemistry.

These and other embodiments, modes, and aspects of the invention are described in more detail in the following description, the examples, and claims set forth below.

MODES OF CARRYING OUT THE INVENTION

As discussed above, modular polyketide synthases (PKSs) are large multifunctional enzyme complexes that are organized into modules, where in addition to a loading domain in the first module, each module carries the domains needed to catalyze the condensation of an extender unit onto a growing polyketide chain. For example, the modular polyketide synthase, 6-deoxyerythronolide B synthase (DEBS), from *Saccharopolyspora erythraea* is an assembly of three large multifunctional proteins—DEBS1, DEBS2, and DEBS3—that catalyze the biosynthesis of the erythromycin macrolactone, 6-deoxyerythronolide B (6-dEB). Each of the three proteins is organized into two modules, and each module carries the catalytic domains needed to incorporate one of six methylmalonyl-CoA extender units onto a growing polypropionate chain (see Cortés et al., 1990, *Nature* 348: 176–178, and Donadio et al., 1991, *Science* 252: 675–679, each of which is incorporated herein by reference). The modular polyketide synthases in general share this organization. Additional examples of such modular PKS include those which synthesize the macrolactone precursors for picromycin, oleandomycin, epothilone, narbomycin, FK-520 and rapamycin. Significant portions of these and other modular PKS have been cloned and sequenced.

It will be evident that the nature of the macrolactone produced will depend on the number of modules in the PKS system, the nature of the starter and of the extender unit added by each module, and, if the extender unit results in a chiral center, the stereochemistry resulting from the condensation or further reaction. The ability to manipulate the PKS genes, both in cell-free systems and in cells transformed with recombinantly manipulated DNA, permits ready control of the number of modules present. In addition, it has been possible to mix and match domains and modules from existing PKS genes to generate novel polyketides. See, for example Khosla, 1997, *Chem. Rev.* 97: 2577–2590; Hopwood, 1997, *Chem. Rev.* 97: 2465–2495; Shen et al., 1995, *J. Amer. Chem. Soc.* 117: 6811–6821; and PCT publication Nos. WO 99/03986 and 97/02358, each of which is incorporated herein by reference. See, also, U.S. Pat. No. 5,672,491.

The present invention provides a more focused approach to controlling the nature of the starter and extender units incorporated, and expands the range of starter and extender unit candidates for incorporation. It also provides extender substrates which can be economically synthesized for incorporation into novel polyketides. These extender substrates include not only those which are incorporated by naturally occurring PKS enzymes, but also "unnatural" extender units which are incorporated only by virtue of manipulation of the PKS genes according to the methods of the present invention. In addition, the invention provides a means to control the stereochemistry of the chiral centers in the resulting polyketide.

EXTENDER UNIT VARIATION AND INCORPORATION

Several recent studies have demonstrated that extender unit specificity can be altered by AT domain substitution, and it is well-established that the extender-unit specificity towards malonyl- or methylmalonyl-CoA is exclusively controlled by the AT domains of the individual modules. It is also known that when methylmalonyl-CoA is the extender unit, only the (2S)-methylmalonyl-CoA enantiomer is incorporated. The present invention has resulted in the identification of an "AT hypervariable region" that controls the acceptance of starter and extender units. As further described below, the AT domain, while controlling the stereochemistry of the extender unit accepted, does not control the resulting chirality of the condensation product.

With regard to the role of AT domains in controlling the nature of extender units, it has been shown that replacement of the AT1 domain of DEBS1+TE with the RAPS AT2 domain results in biosynthesis of the predicted 4-desmethyltriketide lactone (see Oliynyk et al., 1996, *Chem. & Bio.* 3: 833–839, incorporated herein by reference). Similarly, replacement of the individual AT1, AT2, or AT6 domain of DEBS with heterologous AT domains that are specific for malonyl-CoA leads to production of the predicted desmethyl 6-dEB or erythromycin derivative (see Ruan et al., 1997, *J. Bact.* 170:6416–6425; and Liu et al., 1997, *J. Am. Chem. Soc.* 119: 10553–10554, each of which is incorporated herein by reference).

However, the yields of the products generated by these chimeras vary greatly depending on the position of the polyketide chain at which the modified extender unit is incorporated. For example, production of the 10-desmethylerythromycin derivatives, resulting from replacement of the DEBS AT2 domain with a heterologous AT domain specific for malonyl-CoA, is significantly lower than that of the 12-desmethylerythromycin derivative, which results from replacement of the DEBS AT1 domain with a malonyl-CoA-specific AT domain (see Ruan et al., 1997, supra). This suggests that intermediates that are altered at different positions of the polyketide backbone, may be recognized or processed to varying degrees by the modules downstream of the one responsible for the modification. Liu et al. 1997, supra also report that replacement of the final AT domain of DEBS (AT6) with the malonyl-CoA-specific RAPS AT2 domain leads to sizable production of the 2-desmethyl-6-dEB compound. In this case the resulting modified intermediate generated by module 6 does not have to undergo further downstream processing and can simply be directly cyclized by the thioesterase domain.

Sequence analysis of 20 AT domains from DEBS and RAPS led to the identification of signature sequences that could be used to discriminate between malonyl transferases and methylmalonyl transferases (see Haydock et al., 1997, *FEBS* 374: 246–248, incorporated herein by reference). Subsequent studies on the FK-506, rifamycin, and niddamycin (see Motamedi et al., 1997, *Eur. J. Biochem.* 224: 74–80; August et al., 1998, *Chem. & Biol.* 5: 69–79; and Kakavas et al., 1997, *J. Bact.* 179: 7515–7522, each of which is incorporated herein by reference) PKSs have confirmed that the utility of these signature sequences in analyzing naturally occurring PKS modules. The predictive power of these signature sequences is probably due to evolutionary constraints rather than mechanistic ones. The signature sequences are at a location in the AT domains different from that of the hypervariable region described below. They appear to be of diagnostic use only, and are not causative of specificity. Thus, whereas the a priori prediction of substrate specificity of AT domains found in nature can benefit from the above-mentioned signature sequences, the design of AT domains with altered or relaxed substrate specificity will require structure-based and/or combinatorial genetic manipulation of the hypervariable region in accordance with the methods of the present invention.

The structural determinants of extender specificity in the AT domains were identified by the present inventors by constructing hybrid AT domains. Fragments of a malonyl-CoA-specific AT domain were replaced with homologous segments from a methylmalonyl-CoA-specific AT domain, and vice versa. Specifically, replacement of the DEBS AT2 domain by the RAPS AT2 domain in DEBS1+TE leads to the production of approximately 10 mg/mL of the expected 2-desmethyl triketide lactone. By contrast, the same domain swap in the full (6-module) DEBS system results in a considerably lower yield of the corresponding 10-desmethyl 6-dEB (<1 mg/L). This finding supports the suggestion that the heterologous RAPS AT2 domain is fully capable of recruiting a malonyl-CoA extender unit for incorporation onto the growing polyketide chain, and that subsequent processing of the altered intermediate by downstream modules poses as the main obstacle to efficient product formation.

To dissect the role of specific amino acids in controlling AT substrate specificity, experiments were conducted in which several subdomains between selected malonyl- and methylmalonyl-transferases were exchanged. The results showed that a short (20–35 amino acid) C-terminal segment present in all AT domains is the principal determinant of their substrate specificity. The length and amino acid sequence of this segment, varies considerably among the known AT domains and is thus defined herein as the AT "hypervariable region." The present inventors have discovered that the choice of extender units by the PKS modules is influenced by this "hypervariable region", which can be manipulated by mutagenesis to generate novel AT domains possessing relaxed or altered substrate specificity.

To delineate the region of the AT domain that controls extender substrate specificity, a hybrid PKS which contains the RAPS AT2 domain in place of the DEBS AT2 domain in the full (6 module) DEBS system was used as a base. Then, a series of chimeric AT domains were constructed by replacing fragments of this RAPS AT2 domain (which utilizes malonyl-CoA as substrate) with homologous regions from the DEBS AT2 domain (which uses methylmalonyl-CoA). These chimeric AT domains then were inserted in place of the RAPS AT2 domain. Most chimeras thus generated were apparently inactive.

In particular, a 120-bp XhoI-SstI fragment encoding the divergent signature sequence motif described above from the malonyl-CoA-specific RAPS AT2 domain was replaced by a 140-bp fragment encoding the signature sequence motif for the methylmalonyl-CoA-specific DEBS AT2 domain. The resulting recombinant strain did not produce detectable product. However, when a 190-bp PinAI-PstI fragment at the 3'-end of the RAPS AT2 domain was replaced by a homologous 200-bp fragment from the 3'-end of the DEBS AT2 domain, the resulting recombinant strain produced approximately 10 mg/L of the 6-dEB macrolactone.

The 190-bp PinAI-PstI fragment at the 3'-end of the RAPS AT2 domain can be further subdivided into a 63-bp NheI-StyI fragment and a 120-bp StyI-PstI fragment. The recombinant strain, in which the 120-bp RAPS StyI-PstI was replaced by the 110-bp DEBS StyI-PstI fragment in the full DEBS, did not generate any detectable polyketides. On the other hand, the recombinant strain, in which the 63-bp RAPS NheI-StyI fragment was replaced by the 99-bp DEBS NheI-StyI fragment in the full DEBS, produced about 10 mg/L of 6-dEB.

These results demonstrate that the NheI-StyI fragment plays an important role in controlling the substrate specificity of at least one AT domain. A reverse experiment whereby substitution of this segment in a methylmalonyl-AT domain by its counterpart from a malonyl-AT domain would lead to the formation of the expected desmethyl-analog of the natural product was then conducted. As stated above, substitution of DEBS AT6 by RAPS AT2 leads to the biosynthesis of 2-desmethyl-6-dEB in good yield (10 mg/L). Therefore, module 6 of the DEBS was selected for the reverse experiment.

The 84-bp NheI-StyI fragment of the DEBS AT6 domain, which is homologous to the 99-bp NheI-StyI fragment of the DEBS AT2 domain, was replaced by the 63-bp NheI-StyI fragment of the RAPS AT2 domain. The design of this hybrid was based on well-established sequence alignments of AT domains from modular PKSs. The resulting recombinant strain produced the predicted 2-desmethyl 6-dEB (~5 mg/L) as well as comparable amounts of 6-dEB. A mixture of the two compounds is also known to be present in extracts from the recombinant strain previously described (see Liu et al., 1997, supra).

Figure 1:
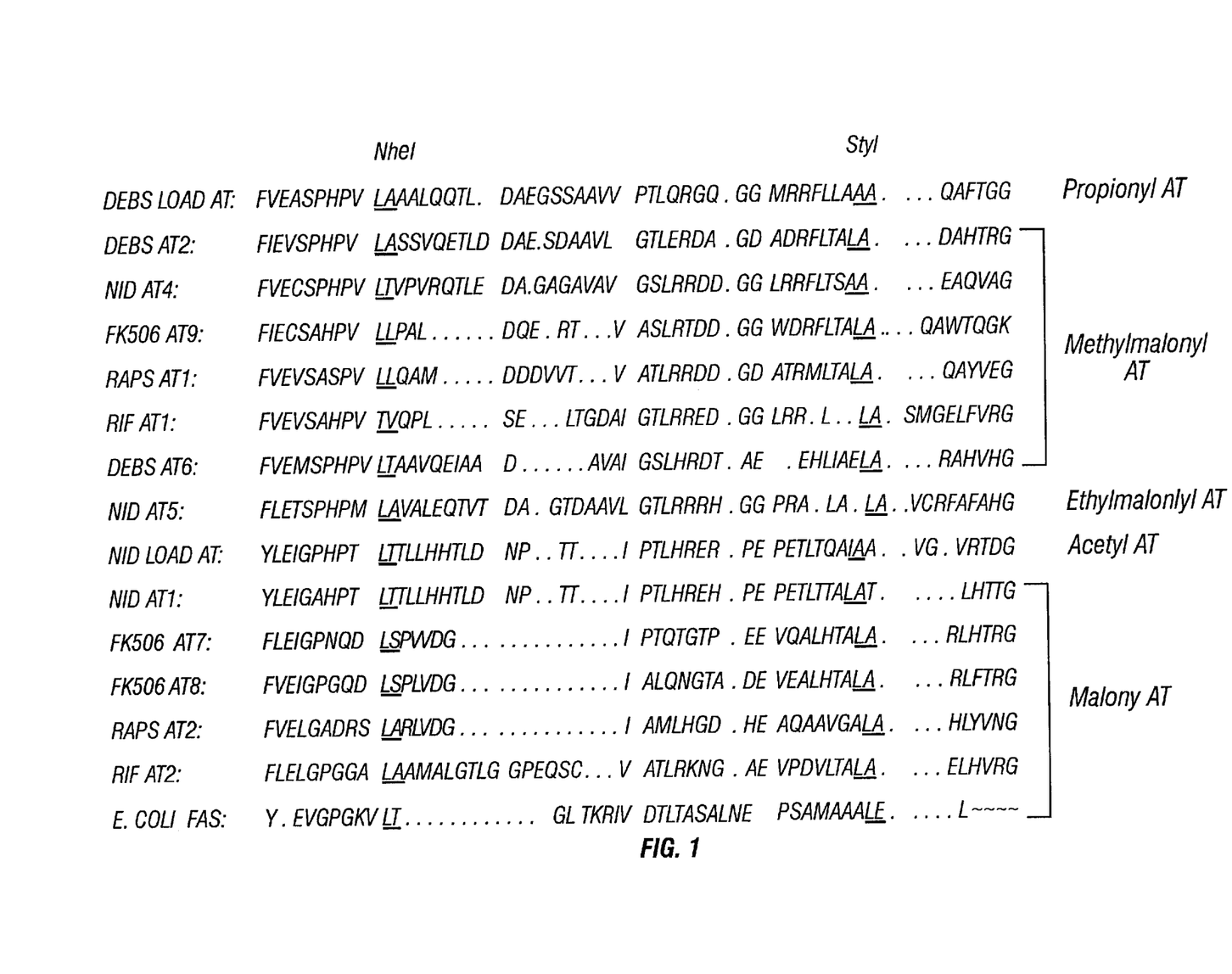
FIG. 1 shows the hypervariable region of a number of illustrative AT domains.

Thus the 33 amino-acid segment encoded by the NheI-StyI fragment of the DEBS AT2 domain, or its counterparts in other AT domains, such as DEBS AT6 and RAPS AT2, are important determinants of specificity for methylmalonyl- or malonyl-CoA substrates. Sequence comparison among analogous segments from these and other known AT domains reveals striking diversity both with respect to length (21–33 residues) and sequence. Illustrative representative sequences of these hypervariable domains are shown in FIG. 1. While a definitive consensus sequence or sequences that universally correlate primary protein structure to substrate specificity cannot as yet be deduced, the corresponding hypervariable region in any AT domain amino acid sequence can be identified by comparison with the illustrative sequences shown in FIG. 1. Most remarkably, this region varies considerably from its counterpart in the crystallographically characterized malonyl transferase of the *E. coli* fatty acid synthase (see Serre et al., 1995, *J. Biol. Chem.* 270: 12961–12964, incorporated herein by reference). Based on an analogy with the immunoglobulins, the substrate specificity of AT domains in modular PKSs can be said to be controlled by a "hypervariable region" located at the C-terminal end of the domain, whose boundary can be defined from sequence comparison, as including 20–35 amino acid residues corresponding to the sequence encoded by the 99-bp NheI-StyI fragment of the DEBS AT2 domain.

Thus, the invention provides a suitable target "hypervariable region" identified in the AT domains of the modular PKS systems which can be manipulated to alter the specificity with respect to extender substrates so that the PKS system can incorporate not only other extenders which are incorporated into wild-type polyketides but also permitting these domains to incorporate extender units which have heretofore not been incorporated into polyketides or are not incorporated into polyketides in native systems. In one aspect, the invention provides a method for altering the specificity of an acyltransferase domain of a polyketide synthase, which method comprises the step of changing the amino acid sequence of the hypervariable region of the AT domain without changing at least a portion of the remaining AT domain amino acid sequence so that the specificity of the AT domain is changed from one naturally occurring starter or extender unit to another. In this embodiment, the known sequences of AT domains with the desired alternative specificity may be used as a guide. In a related embodiment, the invention provides a method for changing the specificity of an AT domain of a PKS to accommodate a starter or extender unit not normally incorporated by a PKS. This method also comprises altering the amino acid sequence of the hypervariable region of the AT domain, for example, by specific or random mutagenesis. In this embodiment, the method optionally further comprises contacting the PKS comprising the altered AT domain with one or more non-naturally incorporated starter or extender units, and identifying whether the altered AT domain can incorporate the tested incorporated starter or extender unit. In related embodiments, the invention provides novel PKS enzymes capable of incorporating non-naturally incorporated starter or extender unit, methods of using them, and novel polyketides produced thereby.

The amino acid sequence of the hypervariable region of an AT domain can be altered by a variety of methods known in the art. If desired, the amino acid sequence may be altered at the protein level by suitable synthesis methods. However, it is much more convenient and efficient to modify the nucleotide sequence encoding the hypervariable region. This can be done either in the context of a fragment of DNA containing only the nucleotides of the hypervariable region, or may be performed on larger portions of the AT domain, the module in which it is contained, or in the context of the entire PKS. Individual modules of a PKS system may be modified so that a variety of extender units is incorporated into the polyketide. Thus, it would be possible to modify the hypervariable regions in the DEBS PKS in only selected modules such as modules 2, 5 and 6 to the exclusion of modifications in the remaining modules. The specificity of each individual AT domain can thus be controlled.

Having constructed a PKS of an arbitrary number of modules with the required specificity, polyketides may be produced conveniently either in a cell-free system or in a recombinantly transformed host by supplying the appropriate starter and extender substrates. In some cases, of course, the substrates will already be present in a host cell; in other cases, it will be necessary to supply them for purposes of the production of the polyketide. Described hereinbelow is a cost effective method to prepare useful substrates to generate the extender units both in cases where the extender unit is naturally incorporated by at least one wild-type PKS and in cases where an extender unit is not found in naturally occurring polyketides.

METHODS AND COMPOSITIONS FOR PROVIDING EXTENDER UNITS

In another embodiment, the present invention provides non-naturally occurring extender substrates for PKS enzymes and methods of making them. In one embodiment, these non-naturally occurring extender substrates are used to make polyketides in a cell-free system and in host cells that do not naturally produce polyketides but which can produce polyketides when provided with a recombinant PKS and one or more novel extender units of the invention.

The extender substrates provided by the invention may result in the incorporation of a subunit normally included in a polyketide made by a wild-type PKS, or may provide for the incorporation of a subunit that is not natively incorporated into any polyketide.

The naturally occurring substrates for both starter and extender subunits are typically coenzyme A thioesters of the relevant carboxylic acids. However, the cost of the required coenzyme A thioesters needed for chain extension is prohibitive to larger scale in vitro synthesis of polyketides or simple in vivo synthesis in organisms such as E. coli that do not naturally synthesize an endogenous supply of the required extender substrate MeMalCoA. A less costly extender unit is key to the realization of preparative scale syntheses of engineered polyketides.

It has been shown that a truncated form of the coenzyme A thioester of a diketide can be incorporated into the growing polyketide chain by modular PKS systems. (See, for example, European application 96/925275.8 and PCT application PCT/US98/14911. This is consistent with the finding that the N-acetyl cysteamine (NAC) thioesters can be incorporated both in vivo and in vitro as primers for polyketide synthesis (see Yue et al., 1987, J. Amer. Chem. Soc. 109: 1253–1257, incorporated herein by reference). These analogs can be taken up by cells from exogenous media, unlike CoA esters, and can be accepted by the desired PKS enzymes. However, whether the time scale of iterative condensations versus initial priming would allow incorporation of extender NAC-thioester substrates was unclear prior to the present invention.

Further, the preparation even of the NAC thioester of methyl malonic acid has not been reported. Malonyl NAC thioester has been described, but without description of its preparation method (see Arnstadt, 1976, Liebigs Ann. Chem., 1976: 843–847, incorporated herein by reference). While the multistep route used to make methylmalonyl coenzyme A (MeMalCoA) via the thiophenyl ester (see Padmakumar et al., 1993, Anal. Biochem. 214: 318–320, incorporated herein by reference) should be able to produce the NAC analog, a shorter sequence in which the difficult monothioesterification of a diacid could be avoided is desirable. The present invention provides such a method which is applicable to extender substrates in general.

Thus, the invention provides extender substrates which are N-acetyl cysteamine thioesters of the formula:

i.e., HOOC—CHR—CONAC (1), wherein R is alkyl (1–8C), alkenyl (1–8C) or alkynyl (1–8C) optionally containing one or more heteroatoms, and optionally substituted with one or more substituents selected from the group consisting of halo, —OR', —SR' and —NR'$_2$, wherein each R' is independently H or alkyl (1–6C) and wherein the substitution is nontoxic to the PKS enzyme. The alkyl, alkenyl, and alkynyl substituents may be straight-chain, branched or cyclic.

R may also be aryl (6–10C), heteroaryl (6–10C) wherein the aromatic system contains one or more nitrogens, or is arylalkyl (7–15C) or heteroarylalkyl (7–15C). These embodiments of R may be substituted as described for the alkyl, alkenyl and alkynyl moieties set forth above. In addition, the aryl and heteroaryl moieties may be substituted by additional alkyl, alkenyl or alkynyl groups in all cases (1–8C) as described above. The substitution in such cases must also be nontoxic to the PKS enzyme.

Preferred embodiments of the compound of formula (1) are those wherein R is lower alkyl (1–4C), lower alkenyl (1–4C) or lower alkynyl (1–4C) optionally substituted with one or two substituents selected from the group set forth above except that each R' is independently H, methyl or ethyl. Also preferred are embodiments wherein R is substituted or unsubstituted phenyl, benzyl, phenylethyl or phenylpropyl. Substitution of these embodiments of R is preferably one or two substituents on the phenyl moiety which are halo, —OH, —OCH$_3$, —NH$_2$, —NHCH$_3$, —N(CH$_3$)$_2$ or lower alkyl (1–4C). Where R includes a heteroaryl moiety, preferred embodiments include pyridine pyrimidine, indole, quinolyn and azulene. Where R is alkyl, alkenyl or alkynyl containing one or more heteroatoms, preferred heteroatoms are O and N and among these, preferred embodiments are cyclic. Thus, preferred embodiments include substituted or unsubstituted cyclohexyl, cyclopentyl, piperidine, piperazine, furan, tetrahydrofuran, and the like.

Especially preferred among compounds of formula (1) are those embodiments wherein R is an unsubstituted alkyl, alkenyl, alkynyl, aryl or arylalkyl, most preferably unsubstituted lower alkyl, lower alkenyl, lower alkynyl, phenyl, benzyl, phenylethyl or phenylpropyl. Also preferred are unsubstituted alkyl, alkenyl, or alkynyl containing one or more heteroatoms or unsubstituted heteroaryl or heteroarylalkyl.

The compounds of formula (1) contain a chiral center. Accordingly, the invention is directed to compounds of formula (1) which may be in the form of racemic mixtures or may be in the form of an isolated enantiomer. Because the AT domains in the PKS systems may be manipulated to relax their substrate specificities, both the R and S forms of the compound of formula (1) are included in the invention. Further, the substituent R may itself contain chiral centers and thus various forms of the compound of formula (1) with respect to its stereoisomers are within the scope of the invention. The invention includes compounds of formula (1) having varying amounts of individual stereoisomers of that formula.

To prepare the compounds of formula (1), Meldrum's acid or an analog thereof is used as a starting material. Meldrum's acid is a commonly used substrate for acylation chemistry, because nucleophilic ring-opening and decarboxylation subsequently yields beta-keto esters (see Oikawa et al., 1978, *J. Org. Chem.* 43: 2087–2088, and Gilbert et al., 1995, *Biorg. Med. Chem. Lett.* 5: 1587–1590, incorporated herein by reference). Direct nucleophilic attack of Meldrum's acid is a common route to various monoesters (see McNab, 1978, *Chem. Soc. Rev.* 7: 345–358, incorporated herein by reference). Surprisingly, treatment of methyl Meldrum's acid with NAC failed to afford the desired thioester. A more reactive nucleophile is required, but the low pKa (4.97; see Pihlaja et al., 1969, *Acta Chem. Scand.* 23: 3003–3010, incorporated herein by reference) of Meldrum's acid prohibited use of preformed thiolates.

Previous work with amines and alcohols (see Rigo et al., 1989, *Tetrahedron Lett.* 30: 3073–3076, incorporated herein by reference) suggested that silylated nucleophiles would permit milder conditions. A trimethylsilylated thiol nucleophile made with catalytic trimethylsilyl triflate (see Sassaman et al., 1990, *Synthesis* 1990: 104–106, incorporated herein by reference) was effective without addition of heat. Both Meldrum's acid and methyl Meldrum's acid were converted to the desired NAC thioesters by treating the starting material with N-acetyl cysteamine in the presence of a trimethylsilyl triflate catalyst in methylene chloride as shown below:

When R is methyl, the data verifying the product are as follows:

($^1$H NMR (400 MHz, CDCl$_3$) delta 9.50 (br s, 1 H), 6.41 (br s, 1 H), 3.63 (q, J=7.0 Hz, 1 H), 3.42-3.34 (m, 2 H), 3.11-2.93 (m, 2 H), 1.99 (s, 3 H), 1.45 (d, J=7.0 Hz, 3 H); $^{13}$C NMR (100 MHz, CDCl$_3$) delta 197.7, 172.8, 172.7, 54.8, 40.1, 29.2, 23.4, 14.7; FAB$^+$ MS (NBA/NaI) calcd. for (C HOSN)H$^+$ 220.0644, observed 220.0641).

INCORPORATION OF NAC THIOESTERS

On a per mole basis, MeMalSNAC is about 4000 times cheaper than the corresponding coenzyme A derivative. (Actually, methyl Meldrum's acid is less expensive per mole than methyl malonic acid.) However, only a five to ten-fold increase in concentration over usual MeMalCoA concentrations (1 mM) was needed to produce approximately the same amount of polyketide product.

MeMalSNAC was used in a reaction with the purified third polypeptide of DEBS (DEBS3+TE). A doubly $^{13}$C-labeled diketide (see Cane et al., 1993, *J. Amer. Chem. Soc.* 115: 522–526, incorporated herein by reference) was employed as a primer so that product formation could easily be identified by $^{13}$C NMR. In fact $^{13}$C NMR of the crude ethyl acetate extract of the enzymatic reaction clearly showed formation of the known triketide lactone, thereby confirming the acceptance of MeMalSNAC as a substrate by the DEBS3+TE system. In addition to the doubly $^{13}$C-labeled unincorporated diketide showing two strong doublets, two doublets with 35 Hz coupling could also be seen that were shifted to the characteristic lactone chemical shifts. The coupling constants remained the same upon going to a higher field strength NMR, thereby ruling out assignment of these peaks to fortuitous singlets coming from large impurities.

CONTROL OF STEREOCHEMISTRY

In 6-dEB, the stereochemistry of the methyl-branched centers arising from the individual condensation reactions is also determined as each successive C$_3$ unit is added. In 6-dEB, the three chiral carbons at the C-2, C-4, and C-10 positions all have the D-methyl configuration, whereas those at the C-6, C-8, and C-12 positions have the L-methyl configuration. The D-methyl configuration is that which would result as expected from the D-carboxylative inversion of the (2S)-methylmalonyl CoA substrates, which are required. The (2R)-methylmalonyl CoA enantiomer is not incorporated. (See Marsden et al., 1994, *Science* 263: 378–380, incorporated herein by reference.) Thus, the pattern observed in the DEBS system is as shown in the table below.

| D-methyl | Generated by molecule | L-methyl | Generated by molecule |
|---|---|---|---|
| C-2 | 6 | C-12 | 1 |
| C-4 | 5 | C-8 | 3 |
| C-10 | 2 | | |

The present invention provides means to control the stereochemistry at these positions or positions where the chirality is controlled by the PKS in other polyketides.

It has been suggested that the PKS system itself is responsible for controlling the stereochemistry at most chiral centers. It has now been found that the AT domains of DEBS do not influence epimerization of the (2S)-methylmalonyl-CoA extender units, and that stereochemical control of the methyl-branched centers generated by DEBS resides in the ketosynthase (KS) domains of the individual modules. The stereochemistry of a polyketide may therefore be controlled by including in the PKS the KS domains that dictate the desired stereochemistry. For example, recombinant PKS enzymes in which a KS domain specifying a first stereochemistry may be replaced by a KS domain specifying a second stereochemistry.

Certain parameters with respect to control of the polyketide stereochemistry are known. Incorporation of deuterated propionate into erythromycin A demonstrated that formation of the D-methyl centers at C-2, C-4, and C-10 of the polyketide chain results directly from decarboxylative inversion of the (2S)-methylmalonyl-CoA substrates (see Cane et al., 1986, *J. Am. Chem. Soc.* 108: 4957–4964, incorporated herein by reference). In the triketide lactone formed by DEBS1+TE, in the presence of (2S)-[2-$^2$H]-methylmalonyl-CoA, H was lost from the C-4 position. The C-4 position in the triketide lactone carries the L-methyl center generated by module 1 corresponding to C-12 in 6-dEB (see Weissman et al., 1997, *Biochemistry* 36: 13849–13855, incorporated herein by reference).

Together, these findings suggest that generation of the L-methyl centers may involve an epimerization step that is catalyzed by DEBS itself. Because construction of the polyketide chain is processive, this epimerization step would have to take place either in the methylmalonyl moiety prior to the condensation step or in the polyketide product immediately following the ketosynthase reaction. Additional evidence bearing on the timing of the epimerization reaction comes from the recent finding that the stereochemistry of beta-ketoreduction is an intrinsic property of the relevant ketoreductase (KR) domains and is independent of both the stereochemistry and the degree of substitution adjacent to the beta-keto group that undergoes reduction (see Kao et al., 1998, *J. Am. Chem. Soc.* 120: 2478–2479, incorporated herein by reference).

If epimerization were indeed to occur before condensation, it is conceivable that the relevant acyltransferase domains (AT) of DEBS might epimerize the enzyme-bound (2S)-methylmalonyl group to the requisite (2R)-methylmalonyl diastereomer prior to the ketosynthase-catalyzed condensations that generate the beta-ketoacyl polyketide intermediates with L-methyl groups in the alpha-position. Although (2S)-methylmalonyl-CoA serves as the sole substrate for the AT domains of DEBS, the expected D-methyl center, generated by decarboxylative inversion of the extender units, is found only in the growing polyketide chains produced by modules 2, 5, and 6. By contrast, the epimeric L-methyl configuration is observed at C-12 and C-8, positions in the erythromycin polyketide generated by modules 1 and 3, respectively. Because the L-methyl configuration at the alpha position of the acyl chain generated by module 4 is certainly due to the reduction of its corresponding alpha-methyl-alpha, beta-unsaturated ester intermediate, it is unknown whether module 4 contains epimerase activity. Notwithstanding this ambiguity, the possible ability of the AT4 domain to epimerize its bound (2S)-methylmalonyl substrate can still be evaluated by alternately replacing the AT1 or AT2 domain of the DEBS1+TE mutant with the AT4 domain. If the AT4 domain were to have no intrinsic epimerase activity, then both of the derived hybrid PKSs would produce the natural (2R, 3S, 4S, 5R)-2,4-dimethyl-3,5-dihydroxy-n-heptanoic acid delta-lactone. On the other hand, if the donor AT4 domain, or one or the other of the replaced AT1 and AT2 domains were able to mediate epimerization, then one of the two hybrid PKSs would be expected to produce a diastereomer.

To test this hypothesis, two chimeric derivatives of DEBS1+TE, in which the AT domains of module 1 (AT1) and of module 2 (AT2) were independently replaced by the AT domain of module 4 (AT4) were constructed. Heterologous expression of DEBS1+TE in *Streptomyces coelicolor* normally results in formation of the triketide (2R, 3S, 4S, 5R)-2,4-dimethyl-3,5-dihydroxy-n-heptanoic acid delta-lactone (see Cortés et al., 1995, *Science* 268: 1487–1489, and Kao et al., 1995, *J. Am. Chem. Soc.* 11: 9105–9106, each of which is incorporated herein by reference). Each of the chimeric proteins, in which either AT1 or AT2 was replaced by AT4, produces the same triketide lactone with unaltered stereochemistry.

From these results, the observed interchangeability of DEBS AT4 with either the AT1 or the AT2 domain in formation of the triketide lactone suggests not only that the donor AT domain retains its catalytic activity upon introduction into another module, but that there is no intrinsic epimerase activity associated with any of these three AT domains. This is consistent with recent reports that replacement of the DEBS KR2 domain with either the KR2 or KR4 domains of the rapamycin PKS results in formation of the 3-epi-triketide lactone, thereby establishing that the configuration of the polyketide hydroxyl groups is controlled directly by the operative KR domain and is not correlated with the stereochemistry or degree of substitution at the adjacent alpha-position (see Kao et al., 1998, *J. Am. Chem. Soc.* 120: 2478–2479, incorporated herein by reference). It has also been shown that replacement of the DEBS ACP3 domain with the DEBS ACP6 domain in a truncated trimodular PKS does not result in alteration of stereochemistry of the relevant methyl-branched centers (see McDaniel et al., 1997, *Chem. & Biol.* 4: 667–674, incorporated herein by reference). Thus, neither the AT, the KR, nor the ACP domain is responsible for the epimerization that results in generation of the L-methyl-branched centers derived from (2S)-methylmalonyl-CoA. The critical epimerase activity is therefore associated directly with the individual KS domains.

It has thus been found that the stereochemistry of the methyl-branched centers of 6-dEB and the corresponding branched centers of other polyketides is controlled by the KS domains of the corresponding modules for those centers. It is thus possible to alter the stereochemistry of a polyketide by modifying the PKS that produces the polyketide to replace a KS domain specifying an undesired stereochemistry with another KS domain that specifies an alternate stereochemistry.

Thus, with respect to the DEBS PKS system, it is clear that the KS1 and KS3 ketosynthase domains will result in an "L-methyl" or corresponding configuration of a polyketide formed from a substituted malonate and KS2, KS5 and KS6 will result in the alternative stereochemistry. In constructing polyketides or libraries thereof, therefore, it is possible to use this information to control the stereochemistry of any position generated from an extender unit containing a chiral center at the α-position (unless the stereochemistry is controlled by reduction of a π-bond as is the case for the stereochemistry at C-6 in DEB). Thus, for any length module PKS, with any choice of extender units, the number of possible variants is enhanced by 2 raised to the power of the number of chiral centers that can be specified in this way. Specifically, for example, the stereochemistry at C-12 of 6-DEB can be altered from the L-methyl configuration to the D-methyl configuration by replacing KS1 with, for example, KS5 of the same PKS system.

The following examples are given for the purpose of illustrating the present invention and should not be construed as limiting the scope of the invention or claims.

EXAMPLE 1

Plasmid Construction

Figure 2A:
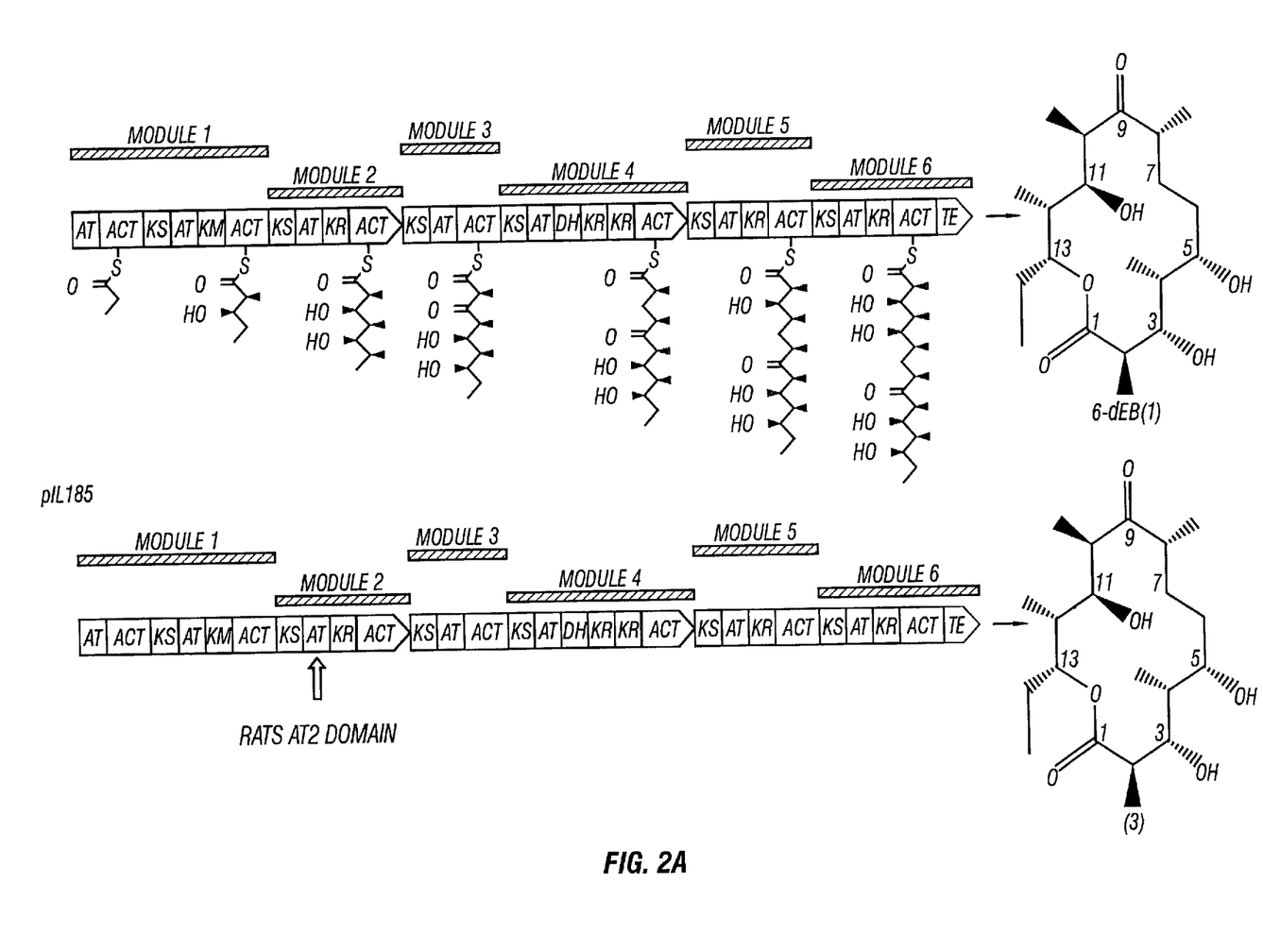
FIG. 2 shows a diagram and products of three modular PKS systems.
Figure 2B:
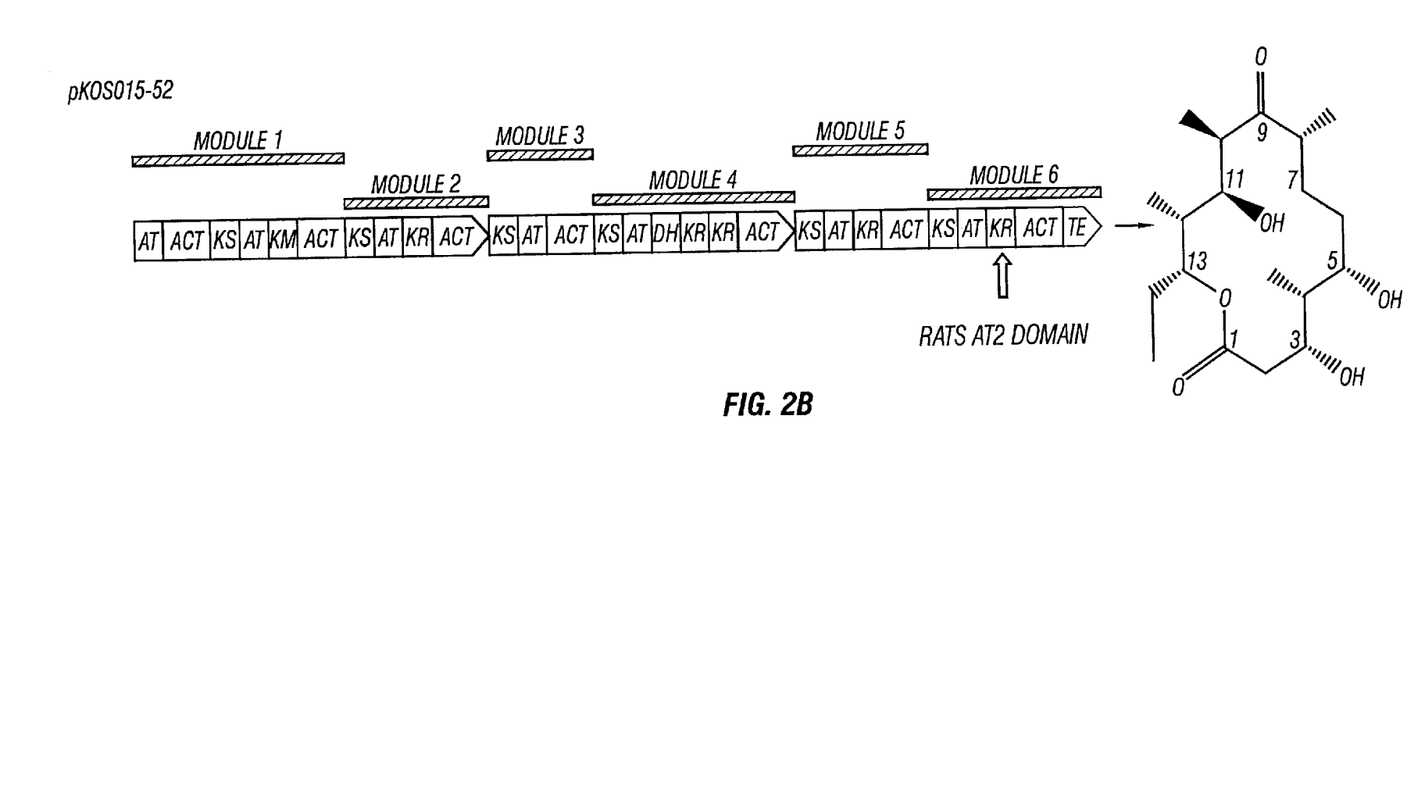

The plasmid pCK7 contains the complete DEBS gene cluster shown in FIG. 2; plasmid pCK12 contains the genes encoding DEBS1+TE. (See Kao et al., 1995, *J. Am. Chem. Soc.* 11: 9105–9106, and Kao et al., 1994, *J. Am. Chem. Soc.* 116: 11612–11613, U.S. Pat. No. 5,672,491, all of which are incorporated herein by reference). Plasmids pJL130 and pJL008 are each derivatives of pCK12 in which a 1.0-kb BamHI-PstI fragment corresponding to either the AT1 domain or the AT2 domain, respectively, is replaced by a 1.0-kb BamHI-PstI fragment corresponding to the AT4 domain of DEBS. pKOS008-51 and pJL185 are, respectively, derivatives of pCK12 and pCK7 in which the 1.0-kb BamHI-PstI fragment corresponding to the entire AT2 domain of DEBS is replaced with a 0.9-kb BglII-PstI fragment corresponding to the intact AT2 domain of the rapamycin polyketide synthase (RAPS).

Plasmid pJL286 is a derivative of pJL185, in which a 120-bp XhoI-SstI fragment of the RAPS AT2 domain encoding the sequence motif suggested to be responsible for malonyl-CoA specificity is excised and replaced with an analogous fragment from the DEBS AT2 domain encoding the corresponding sequence motif suggested for methylmalonyl-CoA specificity (see Haydock et al., 1997, *FEBS* 374: 246–248, incorporated herein by reference).

Plasmid pJL259 is a derivative of pJL185, in which a 190-bp PinAI-PstI fragment encoding the C-terminal region of the RAPS AT2 domain is excised and replaced with its homologous counterpart from the DEBS AT2 domain. Plasmids pJL285 and pJL287 are also derivatives of pJL185, in which either a 63-bp NheI-StyI fragment or a 120-bp StyI-PstI fragment corresponding to a subregion of the RAPS PinAI-PstI fragment, respectively, is replaced with its counterpart from the DEBS AT2 domain. Plasmid pJL305 is a derivative of pCK7 in which a 84-bp NheI-StyI fragment encoding a subregion of the DEBS AT6 domain that is homologous to the one encoded by the NheI-StyI fragment of the DEBS AT2 domain, is replaced with the 63-bp NheI-StyI fragment of the RAPS AT2 domain.

The table below summarizes the plasmids that were described in the preceding paragraph.

| Derived from pCK12 (DEBS1 + TE) | |
| --- | --- |
| pJL130 | AT1 → AT4 |
| pJL008 | AT2 → AT4 |
| pKOS008-51 | AT2 → AT2 (RAPS) |
| Derived from pCK7 (DEBS-6 modules) | |
| pJL185 | AT2 → AT2 (RAPS) |
| pJL305 | AT2 → AT2/AT6 (63 bp NheI/StyI) |
| Derived from pJL185 (DEBS - 6 modules) | |
| pJL286 | AT2 (RAPS) → replace 120 bp XhoI/SstI |
| pJL259 | AT2 (RAPS) → replace 190 bp PinAI/PatI |
| pJL285 | AT2 (RAPS) → 63 bp NheI/StyI |
| pJL287 | AT2 (RAPS) → 120 bp StyI/PstI |

Each of these plasmids was introduced into *S. coelicolor* CH999 (see U.S. Pat. No. 5,672,491, incorporated herein by reference) via transformation, and the polyketide products were purified from the resulting transformants according to methods previously described (see Kao et al., 1994, *J. Am. Chem. Soc.* 116: 11612–11613, incorporated herein by reference).

EXAMPLE 2

Analysis of Recombinant Strains

The recombinant strains, CH999/pJL130 and CH999/pJL008, both synthesized a triketide identical to that produced by the parent DEBS1+TE strain. The stereochemistry of the products was established by $^1$H NMR spectroscopy and comparison of the data with that for authentic compound.

The recombinant strain, CH999/pKOS008-51 produced 2-desmethyl-triketide lactone. This novel metabolite was produced at ~10 mg/L, which is half that of the production levels of the parent triketide lactone (~20 mg/L). The structure of this product was confirmed by $^1$H and $^{13}$C NMR spectroscopy.

Similarly, the recombinant strain, CH999/pJL185 putatively produced 10-desmethyl 6-dEB, however, this was generated in amounts insufficient for exhaustive spectroscopic characterization (<1 mg/L). Its existence in the fermentation broth was detected by AP-CI mass spectroscopy (M+H$^+$=373, M–H$_2$O+H$^+$=355, M–2H$_2$O+H$^+$=337). This result is consistent with that described in Ruan et al., 1997, *J. Bact.* 170: 6416–6425 where the corresponding 10-desmethyl analog of erythromycin was produced by similar AT swaps into DEBS in the native erythromycin producer *Saccharopolyspora erythraea*. Although the exact titers were not reported, Ruan et al. reported the isolation of a few milligrams of the product from a 27 L fermentation, suggesting that the titer of this novel erythromycin in *S. erythraea* was considerably lower than that of the parent natural product in the same host. (This is shown diagrammatically in FIG. (2).)

The recombinant strains, CH999/pJL286, CH999/pJL259, CH999/pJL285, and CH999/pJL287, contained hybrid RAPS/DEBS AT2 domains. Of the four mutants, CH999/pJL286 and CH999/pJL287 did not produce any detectable polyketides. CH999/pJL259 and CH999/pJL285 both produced approximately 10 mg/L of the 6-dEB macrolactone. The structure of this product was again confirmed by $^1$H NMR spectroscopy. No 10-desmethyl-6-dEB could be detected.

Likewise, the recombinant strain, CH999/pJL305 which carries a plasmid where the AT6 domain of the 6-module DEBS system was replaced with a chimeric DEBS/RAPS domain produced both 6-dEB and the 2-desmethyl 6-dEB in comparable amounts (~5 mg/L). The structures were also confirmed by $^1$H NMR.

The invention having now been described by way of written description and examples, those of skill in the art will recognize that the invention can be practiced in a variety of embodiments and that the foregoing description and examples are for purposes of illustration and not limitation of the following claims.

What is claimed is:

1. A method of producing a polyketide with an inverted chirality at a chiral center generated by the incorporation of α-substituted malonyl extender unit, which method comprises obtaining a polyketide synthase in which the ketosynthase (KS) domain responsible for generating said chiral center is substituted with a second KS domain that generates the opposite chirality in a polyketide synthase module.

2. The method of claim 1 wherein said polyketide synthase module is included in a complete polyketide synthase for a naturally occurring polyketide, and wherein only one KS domain is substituted.

3. The method of claim 2 wherein said polyketide synthase is a 6-dEB polyketide synthase.

4. The method of claim 1 wherein the extender unit is a methylmalonyl coenzyme A.

5. The method of claim 2 wherein the extender unit is a methylmalonyl coenzyme A.

6. The method of claim 1 wherein the first KS domain is the KS domain of module 2, 5 or 6 of 6-dEB polyketide synthase.

7. The method of claim 1 wherein said second KS domain is the KS domain of module 1 or 3 of a 6-dEB polyketide synthase.

* * * * *